(12) United States Patent
Ngwa et al.

(10) Patent No.: US 10,835,604 B2
(45) Date of Patent: Nov. 17, 2020

(54) BIOMATERIALS FOR COMBINED RADIOTHERAPY AND IMMUNOTHERAPY OF CANCER

(71) Applicants: Northeastern University, Boston, MA (US); Dana-Farber Cancer Institute, Inc., Boston, MA (US); The Brigham and Women's Hospital, Inc., Boston, MA (US)

(72) Inventors: Wilfred Ngwa, Orlando, FL (US); Rajiv Kumar, Malden, MA (US); Gerassimos Makrigiorgos, Chestnut Hill, MA (US); Srinivas Sridhar, Newton, MA (US); Stephanie Dougan, Boston, MA (US)

(73) Assignees: Northeastern University, Boston, MA (US); Dana-Farber Cancer Institute, Inc., Boston, MA (US); The Brigham and Women's Hospital, Inc., Boston, MA (US)

(*) Notice: Subject to any disclaimer, the term of this patent is extended or adjusted under 35 U.S.C. 154(b) by 335 days.

(21) Appl. No.: 15/752,099

(22) PCT Filed: Aug. 15, 2016

(86) PCT No.: PCT/US2016/046992
§ 371 (c)(1),
(2) Date: Feb. 12, 2018

(87) PCT Pub. No.: WO2017/027874
PCT Pub. Date: Feb. 16, 2017

(65) Prior Publication Data
US 2018/0271978 A1  Sep. 27, 2018

Related U.S. Application Data

(60) Provisional application No. 62/204,861, filed on Aug. 13, 2015.

(51) Int. Cl.
*A61K 41/00* (2020.01)
*A61N 5/10* (2006.01)
(Continued)

(52) U.S. Cl.
CPC .......... *A61K 41/0038* (2013.01); *A61K 39/00* (2013.01); *A61K 47/6923* (2017.08);
(Continued)

(58) Field of Classification Search
CPC .... A61N 5/1001–1029; A61K 41/0038; A61K 41/0052
See application file for complete search history.

(56) References Cited

U.S. PATENT DOCUMENTS 4,779,806 A   10/1988 Langer et al.
6,399,103 B1   6/2002 Yamagata et al.
(Continued)

FOREIGN PATENT DOCUMENTS

EP   2 555 800 A1   2/2013
WO   WO 2014/188420 A1   11/2014
WO   WO 2016/015044 A1   1/2016

OTHER PUBLICATIONS

PCT/US2016/46992, Oct. 31, 2016, International Search Report and Written Opinion.
PCT/US2016/46992, Feb. 22, 2018, International Preliminary Report on Patentability.
International Search Report and Written Opinion dated Oct. 31, 2016 in connection with International Application No. PCT/US2016/046992.
(Continued)

*Primary Examiner* — Thaddeus B Cox
(74) *Attorney, Agent, or Firm* — Wolf, Greenfield & Sacks, P.C.

(57) ABSTRACT

Compositions and methods for the radiological and immunotherapeutic treatment of cancer are provided. Metallic nanoparticles conjugated with an immunoadjuvant are dispersed within a biodegradable polymer matrix that can be implanted in a patient and released gradually. The implant may be configured as, or be a component of, brachytherapy
(Continued)

spacers and applicators, or radiotherapy fiducial markers. The composition may be combined with marginless radiotherapy, allowing for lower doses of radiation and enhancing the immune response against cancer, including at non-irradiated sites.

20 Claims, 7 Drawing Sheets

(51) Int. Cl.
  *A61K 47/69*  (2017.01)
  *A61K 49/04*  (2006.01)
  *A61K 39/00*  (2006.01)
  *C07K 16/28*  (2006.01)
  *A61N 5/06*  (2006.01)
  *A61N 7/00*  (2006.01)

(52) U.S. Cl.
  CPC ...... *A61K 47/6929* (2017.08); *A61K 49/0428* (2013.01); *A61N 5/1007* (2013.01); *C07K 16/2878* (2013.01); *A61N 5/062* (2013.01); *A61N 7/00* (2013.01); *A61N 2005/1019* (2013.01); *A61N 2005/1089* (2013.01); *A61N 2005/1098* (2013.01)

(56) References Cited

U.S. PATENT DOCUMENTS

| | | | |
|---|---|---|---|
| 2008/0177179 | A1 | 7/2008 | Stubbs et al. |
| 2009/0110644 | A1* | 4/2009 | Margel ............... A61K 47/6921 424/9.322 |
| 2009/0186060 | A1 | 7/2009 | Hainfeld et al. |
| 2010/0183727 | A1* | 7/2010 | Iannacone ............... A61P 35/00 424/489 |
| 2011/0263923 | A1 | 10/2011 | Lamoureux et al. |
| 2012/0083761 | A1* | 4/2012 | Malecki ............. A61K 41/0038 604/500 |
| 2012/0171292 | A1* | 7/2012 | Sailor ..................... A61P 31/16 424/490 |
| 2012/0220921 | A1* | 8/2012 | Chen ....................... A61P 35/00 604/20 |
| 2013/0017265 | A1 | 1/2013 | Farokhzad et al. |
| 2013/0225901 | A1 | 8/2013 | Krishnan et al. |
| 2014/0086869 | A1* | 3/2014 | Chen .................. A61K 39/0011 424/85.5 |
| 2014/0193488 | A1 | 7/2014 | Kim et al. |
| 2014/0193506 | A1* | 7/2014 | Shams .................... A61P 37/04 424/499 |
| 2014/0220143 | A1 | 8/2014 | Dhar et al. |
| 2016/0161475 | A1* | 6/2016 | Chiu ...................... C09K 11/06 506/9 |

OTHER PUBLICATIONS

International Preliminary Report on Patentability dated Feb. 22, 2018 in connection with International Application No. PCT/US2016/046992.
Almeida et al., Gold nanoparticle mediated cancer immunotherapy. Nanomedicine: Nanotechnology, Biology, and Medicine. 2014;10:503-514.
Barker et al., The Tumour Microenvironment after Radiotherapy: Mechanisms of Resistance and Recurrence. Nat Rev Cancer. Jul. 2015;15(7):409-25.
Demaria et al., The Optimal Partnership of Radiation and Immunotherapy: from Preclinical Research Studies to Clinical Translation. Radiation Research. 2014;182(2):170-181.
Fan et al., Nanoparticle Drug Delivery Systems Designed to Improve Cancer Vaccines and Immunotherapy. Vaccines. 2015;3:662-85.
Formenti et al., Pilot trial of radiation therapy and GM-CSF in metastatic cancer: abscopal responses. International J. Radiation Oncology Biology Physics. 2012;84(3):S178.
Formenti et al., Systemic effects of local radiotherapy. Lancet Oncol. Jul. 2009;10(7):718-26.
Golden et al., An Abscopal Response to Radiation and Ipilimumab in a Patient with Metastatic Non-Small Cell Lung Cancer. Cancer Immunology Research. American Association for Cancer Research. Dec. 2013; 1(6):365-72.
Haikerwal et al., Building immunity to cancer with radiation therapy. Cancer Letters. 2015;368:198-208.
Hodge et al., Synergizing Radiation Therapy and Immunotherapy for Curing Incurable Cancers: Opportunities and Challenges. Oncology (Williston Park). Aug. 2008; 22(9):1064-84.
Kotagiri et al., Breaking the depth dependency of phototherapy with Cerenkov radiation and low-radiance-responsive nanophotosensitizers. Nature Nanotechnology. Apr. 2015;10:370-9.
Kumar et al., Localized tumor delivery of radiosensitizers and chemotherapeutics using 'INCeRT' implants. Molecular Cancer Therapeutics. 2013;12:A82.
Kumar et al., Nanoparticle-Based Brachytherapy Spacers for Delivery of Localized Combined Chemoradiation Therapy. International Journal of Radiation Oncology Biology Physics. 2015:91(2):393-400.
Kumar et al., Third generation gold nanoplatform optimized for radiation therapy. Translational Cancer Research. Aug. 2013;2(4):228-239.
Ngwa et al., Targeted radiotherapy with gold nanoparticles: current status and future perspectives. Nanomedicine. 2014;9(7):1063-82.
Ouyang et al., Nanoparticle-aided external beam radiotherapy leveraging Cerenkov effect. Phys Med. Jul. 2016;32(7):944-947.
Zaharoff et al., Intratumoral Immunotherapy of Established Solid Tumors with Chitosan/IL-12. J Immunother. Sep. 2010;33(7):697-705.
EP 16836024.6, Feb. 28, 2019, Extended European Search Report.

* cited by examiner

BIOMATERIALS FOR COMBINED RADIOTHERAPY AND IMMUNOTHERAPY OF CANCER

CROSS REFERENCE TO RELATED APPLICATIONS

This application is a national stage filing under 35 U.S.C. § 371 of International Application PCT/US2016/046992, filed Aug. 15, 2016, and entitled "BIOMATERIALS FOR COMBINED RADIOTHERAPY AND IMMUNO-THERAPY OF CANCER" which claims the benefit under 35 35 U.S.C. § 119(e) of U.S. Provisional Application No. 62/204,861 filed 13 Aug. 2015 and entitled "Priming Radiotherapy and Immunotherapy Eluter (PRImEr)", the contents of which are incorporated herein by reference in their entireties.

STATEMENT REGARDING FEDERALLY SPONSORED RESEARCH OR DEVELOPMENT

This invention was made with government support under grant number K01 CA172478 awarded by The National Institutes of Health. The government has certain rights in the invention.

BACKGROUND

Cancer is a leading cause of death worldwide. About 90 percent of cancer deaths are caused by metastasis, which is the spread of the cancer to other parts of a patient's body, making effective treatment difficult. Currently, radiotherapy is used in the treatment of over 50% of cancer patients, either by itself or in combination with other treatment approaches, such as surgery or chemotherapy. Although highly effective for inflicting damage on tumor cells, the specificity of radiation therapy is derived mainly from the geometric restriction of radiation beams. Sparing of healthy tissues and organs from radiation can be particularly challenging when treating tumors that are located in deep-seated anatomical locations. There is pressing need for strategies to intensify the tumor damage without adding additional risk to the healthy tissue.

In current radiotherapy practice, radiotherapy biomaterials (such as brachytherapy spacers and radiotherapy fiducial markers) are routinely implanted into tumors of solid tissues to guide radiotherapy treatment. The fiducials are essential to localize the tumor and target the radiation, but provide no direct therapeutic benefit. Recently, it has been proposed that fiducials and brachytherapy spacers offer an opportunity for in situ delivery of drugs as part of minimally invasive radiation therapy procedures that are currently routine.

SUMMARY OF THE INVENTION

The present invention provides compositions and methods for use in the combined radiological and immunological therapy of cancer. The compositions include "smart" biomaterials that can replace implanted inert materials currently used in radiological therapy and diagnosis applications.

One aspect of the invention is a composition for use in radiological diagnosis and/or therapy of cancer. The composition includes metallic nanoparticles conjugated with an immunoadjuvant. The nanoparticles are dispersed within a biodegradable polymer matrix. In some embodiments, the nanoparticles include, or consist of, gold, titanium oxide, iron oxide, zinc oxide, platinum, or gadolinium. In some embodiments, the nanoparticles are radiopaque. In some embodiments, the nanoparticles have a size from about 2 nm to about 15 nm. In some embodiments, the nanoparticles are in the form of spheres, rods, cubes, ellipsoids, core-shell structures, or irregularly shaped structures.

In some embodiments, the immunoadjuvant is selected from the group consisting of granulocyte-macrophage colony-stimulating factor (GM-CSF), anti-CD40 antibodies, programmed death 1 (PD-1) receptor antibodies, anti-cytotoxic T-lymphocyte antigen 4 (CTLA-4) antibodies, glucocorticoid-induced tumor necrosis factor receptor (GITR) antibodies, OX40 antibodies, T-cell immunoglobulin and mucin-domain containing-3 (TIM3) antibodies, lymphocyte activation gene 3 (LAG3) antibodies, carcinoembryonic antigen-related cell adhesion molecule (CEACAM) antibodies, interleukin-12 (IL-12), Toll-like receptor (TLR) ligands, stimulator of interferon genes (STING) agonists and combinations thereof.

In some embodiments, the biodegradable polymer matrix includes a polymer selected from the group consisting of polylactide, polyglycolide, polylactide co-glycolide, polyester amides of glycolic or lactic acids, poly(N-isopropylacrylamide), polygalactin, polydioxanone, polyester, polyacrylate, polymethacrylate, polyvinyl alcohol, polyether, polyamine, chitosan, silk, and combinations thereof. In an embodiment, the composition is injectable or implantable in a patient. In some embodiments, a polymer, mixture of polymers, and/or degree of cross-linking of the polymer(s) are selected to provide a desired time course of degradation in the patient and corresponding time course of release of the metallic nanoparticles from the composition.

In some embodiments, the nanoparticles are targeted to bind tumor cells by the inclusion of one or more targeting moieties. The targeting moieties can be selected from the group consisting of folic acid, antibodies, including single-chain variable fragment antibodies, ligands for an epidermal growth factor receptor, human protein transferrin, RGD peptides, small molecules having an affinity for tumor cells, hyaluronic acid, riboflavin, PSMA aptamers, and galactose derivatives.

In some embodiments, the composition is injectable or implantable in a patient. In certain embodiments, the instant composition is configured as, or is a component of, a brachytherapy spacer, a radiotherapy fiducial marker, a balloon applicator, a brachytherapy applicator, a transponder (e.g., BEACON transponder), or a gel.

In some embodiments the composition further includes an antitumor agent. In certain embodiments, the antitumor agent is selected from the group consisting of docetaxel, paclitaxel, gemcitabine, cisplatin, doxorubicin, small molecule signaling pathway inhibitors including PI3K inhibitors, PARP inhibitors, and PI3K/AKT/mTOR pathway inhibitors, and combinations thereof.

Another aspect of the invention is a method of treating cancer. The method includes injecting or implanting a composition as described above, or a device including the composition, into a tumor or into a region including tumor cells, in a patient in need thereof. In some embodiments the composition forms, or is included within, a device that serves as a brachytherapy spacer, radiotherapy fiducial marker, balloon applicator, brachytherapy applicator, beacon, or gel. In some embodiments, the method further includes performing radiation therapy on the patient. In some embodiments, the method further includes administering chemotherapy to the patient. In some embodiments, brachytherapy is performed, and an implanted brachytherapy spacer includes the above-described composition. In some embodiments, external beam radiation therapy is performed, including implanting a fiducial marker that includes the above-described composition. In some embodiments a composition including gold nanoparticles is implanted or injected, and radiation therapy is subsequently performed, which produces electrons by the photoelectric effect, the electrons having or enhancing a tumor cell killing effect. In other embodiments, the composition includes titanium nanoparticles, and the radiation therapy produces Cherenkov radiation, the Cherenkov radiation having or enhancing a tumor cell killing effect. In some embodiments, the method is more effective at killing tumor cells than a method including systemic or local administration of an immunoadjuvant that is not bound to nanoparticles, together with radiation therapy. In some embodiments, the method produces an abscopal effect, wherein tumor cells that have not been irradiated are killed, due to activation of the immune system by the implanted or injected composition. In some embodiments, the dose of radiation is less than would be administered for ordinary radiation therapy alone, due to the use of marginless radiotherapy or due to activation of the immune system by the immunoadjuvant present in a composition of the invention. In some embodiments, the radiation therapy treatment planning or segmentation is marginless or obviates the need for margins including clinical target volume, internal target volume or planning target volume segmentation/contouring. In some embodiments, the patient's immune response against the tumor or tumor cells is enhanced. In some embodiments, the method further includes applying acoustic radiation, such as ultrasound, to the patient following injection or implantation, and in the vicinity of the injected or implanted composition, so as to accelerate degradation of the biodegradable polymer of the composition. In some embodiments, the cancer is pancreatic cancer, lung cancer, prostate cancer, breast cancer, colorectal cancer, liver cancer, cervical cancer, or other gynecologic cancers. In some embodiments, the cancer is metastatic cancer.

The invention can be further summarized by the following listing of embodiments.

1. A composition for use in radiological diagnosis and/or therapy of cancer, the composition comprising metallic nanoparticles conjugated with an immunoadjuvant, the nanoparticles dispersed within a biodegradable polymer matrix.
2. The composition of embodiment 1, wherein the nanoparticles comprise or consist of gold, titanium oxide, iron oxide, zinc oxide, platinum, or gadolinium.
3. The composition of embodiment 1 or embodiment 2, wherein the nanoparticles are radioopaque.
4. The composition of any of the preceding embodiments, wherein the nanoparticles have a size from about 2 nm to about 15 nm.
5. The composition of any of the preceding embodiments, wherein the immunoadjuvant is selected from the group consisting of granulocyte-macrophage colony-stimulating factor (GM-CSF), anti-CD40 antibodies, programmed death 1 (PD-1) receptor antibodies, anti-cytotoxic T-lymphocyte antigen 4 (CTLA-4) antibodies, glucocorticoid-induced tumor necrosis factor receptor (GITR) antibodies, OX40 antibodies, T-cell immunoglobulin and mucin-domain containing-3 (TIM3) antibodies, lymphocyte activation gene 3 (LAG3) antibodies, carcinoembryonic antigen-related cell adhesion molecule (CEACAM) antibodies, interleukin-12 (IL-12), Toll-like receptor (TLR) ligands, Stimulator of interferon genes (STING) agonists, and combinations thereof.
6. The composition of any of the preceding embodiments, wherein the biodegradable polymer matrix comprises a polymer selected from the group consisting of polylactide, polyglycolide, polylactide co-glycolide, polyester amides of glycolic or lactic acids, poly(N-isopropylacrylamide), polygalactin, polydioxanone, polyester, polyacrylate, polymethacrylate, polyvinyl alcohol, polyether, polyamine, chitosan, silk, and combinations thereof.
7. The composition of any of the preceding embodiments that is injectable or implantable in a patient.
8. The composition of embodiment 7 that is configured as, or is a component of, a brachytherapy spacer, a radiotherapy fiducial marker, a balloon applicator, a brachytherapy applicator, a transponder, or a gel.
9. The composition of embodiment 8, wherein the composition is configured as an implant, and the implant size is from about 3 mm to about 5 mm in length and from about 0.5 mm to about 1.5 mm in diameter.
10. The composition of any of the preceding embodiments, wherein the nanoparticles are in the form of spheres, rods, cubes, ellipsoids, or core-shell structures.
11. The composition of any of the preceding embodiments, wherein the nanoparticles are further conjugated to a targeting-moiety, such as a targeting-moiety being selected from the group consisting of folic acid, antibodies including single-chain variable fragment antibody, ligands for an epidermal growth factor receptor, transferrin, an RGD peptide, tumor-specific small molecules, hyaluronic acid, riboflavin, PSMA aptamers, galactose derivatives, and combinations thereof.
12. The composition of any of the preceding embodiments further comprising an antitumor agent, such as an antitumor agent selected from the group consisting of docetaxel, paclitaxel, gemcitabine, cisplatin, doxorubicin, small molecule signaling pathway inhibitors including PI3K inhibitors, PARP inhibitors, and PI3K/AKT/mTOR pathway inhibitors, and combinations thereof.
13. A method of treating cancer, the method comprising injecting or implanting the composition of embodiment 1 or a device comprising said composition into a tumor or into a region comprising tumor cells in a patient in need thereof.
14. The method of embodiment 13, wherein a brachytherapy spacer, radiotherapy fiducial marker, a balloon applicator, a brachytherapy applicator, a transponder, or gel comprising the composition is injected or implanted.
15. The method of embodiment 13 or embodiment 14, further comprising performing radiation therapy on the patient.
16. The method of embodiment 15, wherein brachytherapy is performed, and an implanted brachytherapy spacer comprises said composition.
17. The method of embodiment 15, wherein external beam therapy is performed, and an implanted fiducial marker comprises said composition.
18. The method of any of embodiments 15-17, wherein said composition comprises gold nanoparticles, and the radiation therapy produces electrons by a photoelectric effect.
19. The method of any of embodiments 15-18, wherein said composition comprises titanium oxide nanoparticles, and the radiation therapy produces Cherenkov radiation.
20. The method of any of embodiments 15-19, wherein the method is more effective at killing tumor cells than a method comprising administration of said immunoadjuvant in non-conjugated form and radiation therapy.
21. The method of any of embodiments 13-20 that produces an abscopal effect.

22. The method of any of embodiments 15-21, wherein the dose of radiation is less than would be administered for radiation therapy alone.

23. The method of any of embodiments 15-22, wherein the radiation therapy treatment planning or segmentation is marginless or obviates the need for margins including clinical target volume, internal target volume or planning target volume segmentation/contouring.

24. The method of any of embodiments 13-23, wherein the patient's immune response against said tumor or tumor cells is enhanced.

25. The method of any of embodiments 13-24, further comprising applying electromagnetic or acoustic waves to the patient following injection or implantation, so as to accelerate or activate degradation of the biodegradable polymer of said composition.

26. The method of any of embodiments 13-25, wherein the cancer is pancreatic cancer, lung cancer, prostate cancer, breast cancer, colorectal cancer, liver cancer, cervical cancer and other gynecologic cancers.

27. The method of any of embodiments 13-26, wherein the cancer is metastatic cancer.

BRIEF DESCRIPTION OF THE DRAWINGS

FIG. 1A shows how the composition releases metallic nanoparticles conjugated with an immunoadjuvant, thereby recruiting antigen presenting cells which migrate to lymph nodes where they activate CD8+ T cells that become activated, resulting in killing tumor cells both at the primary tumor and at metastatic sites. FIG. 1B shows that radiation therapy in the presence of gold nanoparticles released from the composition can result in killing of tumor cells through photoelectrons released from the gold nanoparticles. FIG. 1C shows an exemplary time course of release of immunoadjuvant (smooth saturating curve), while radiation therapy is given periodically (peaks). FIG. 1D shows an implant, and FIG. 1E shows an immunoadjuvant-conjugated nanoparticle.

FIG. 2A shows that the spacer is radiopaque and well defined on day 1 post-implantation. FIG. 2B shows the spacer on day 4 post-implantation. The spacer has become smaller and less radioopaque. FIG. 2C shows the spacer on day 6 post-implantation. Its size and radioopacity have further decreased significantly due to the gradual release of the nanoparticles from the polymer matrix. FIG. 2D shows that after 8 days the spacer has completely degraded and disappeared.

DETAILED DESCRIPTION OF THE INVENTION

Figure 1A:
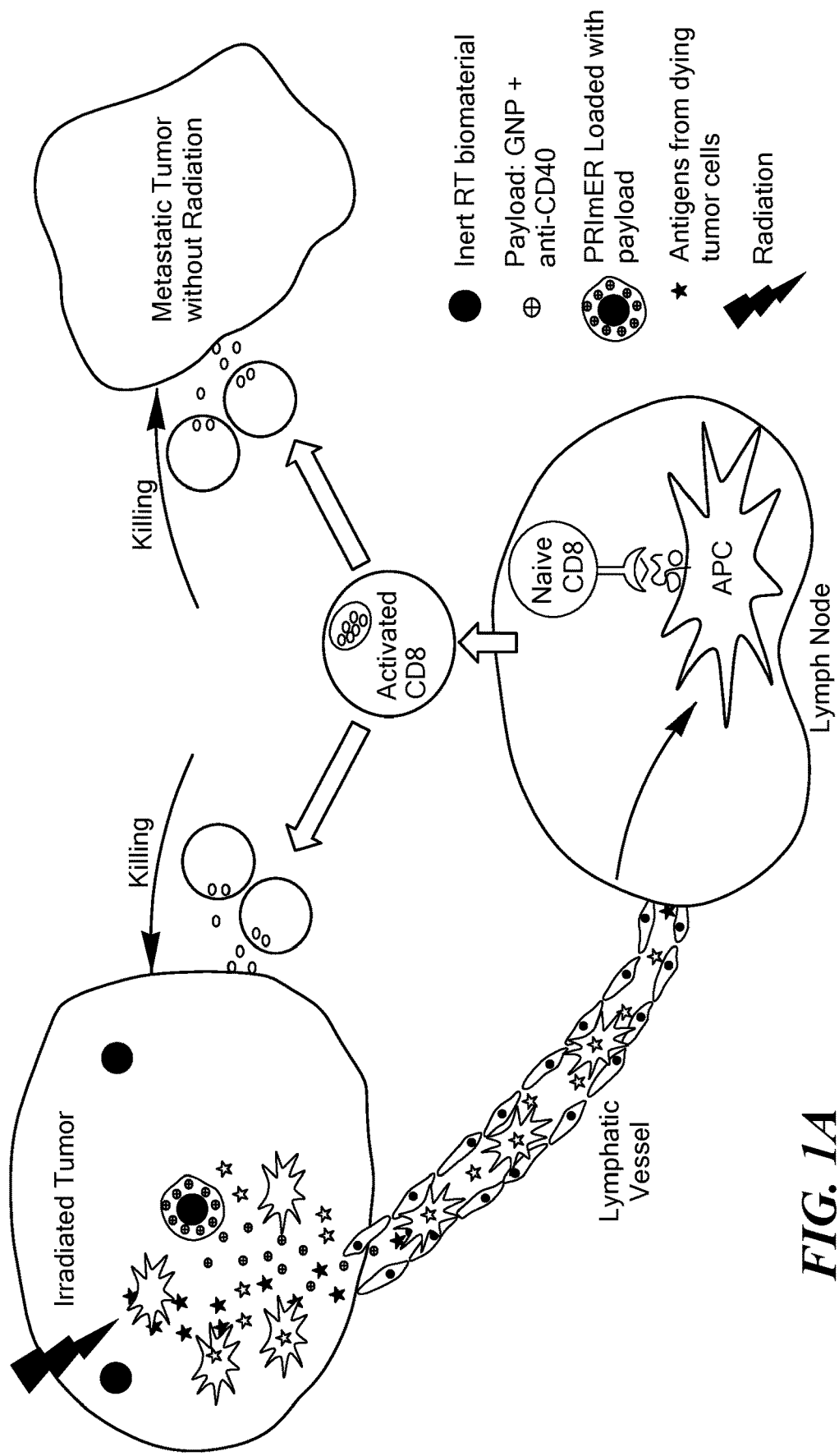
FIGS. 1A-1C show schematic representation of a process of enhancing radiation therapy by the placement of a composition of the invention within a tumor.
Figure 1B:
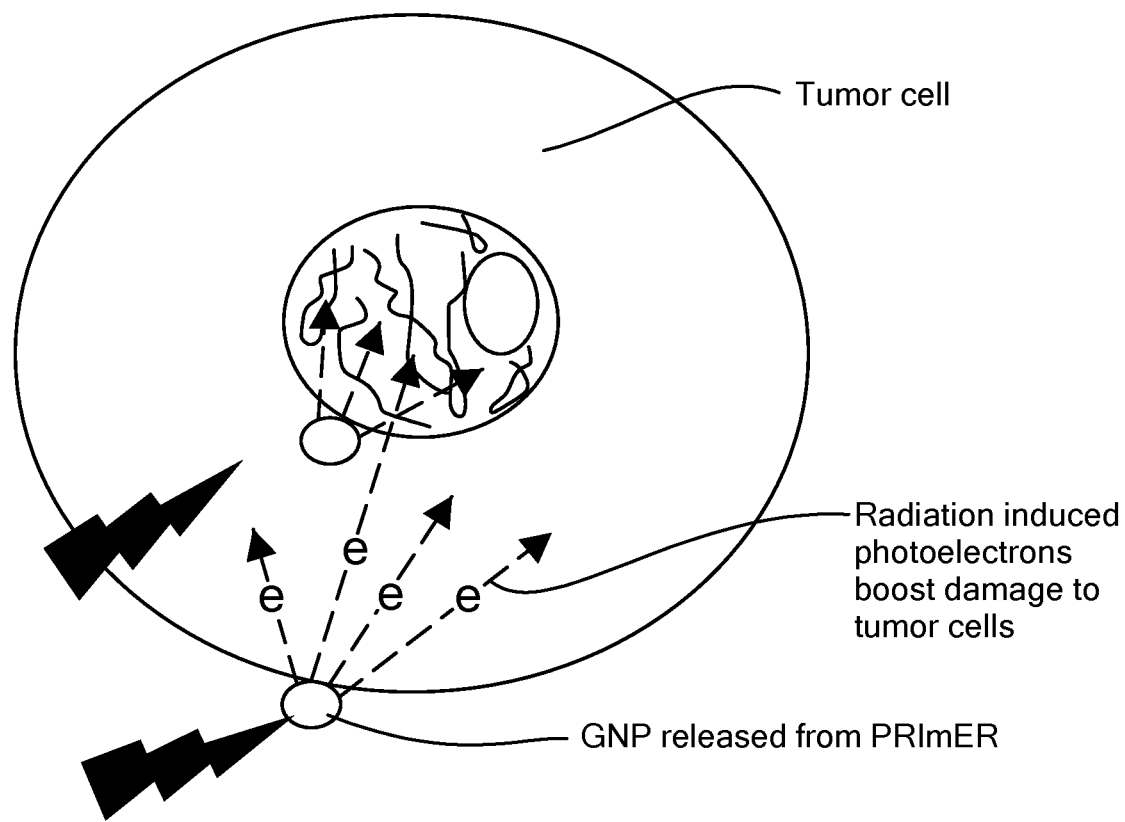
Figure 1C:
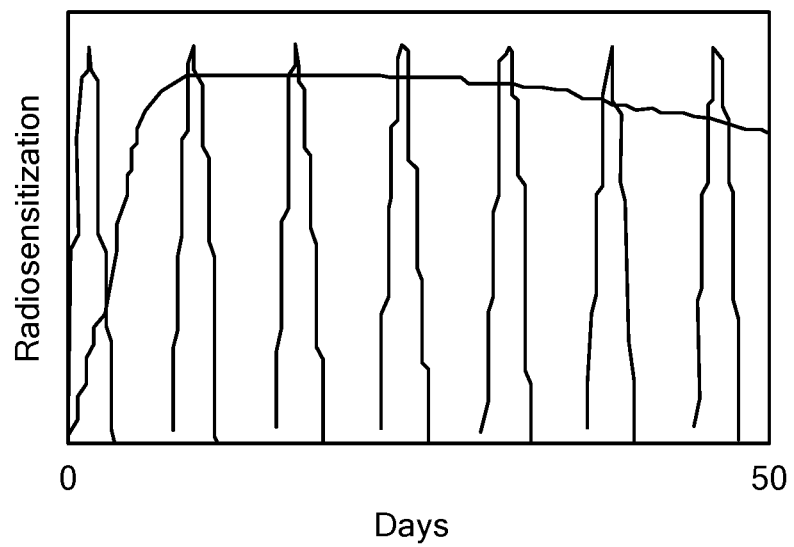

The present invention provides compositions and methods for the radiological and immunological therapy of cancer. A key aspect of the invention is the use of metallic nanoparticles conjugated with an immunoadjuvant agent. The nanoparticles are dispersed within a biodegradable polymer matrix that slowly breaks down when implanted within the body of a patient, releasing the nanoparticles. FIG. 1A. Release of the nanoparticles can be programmed to occur within a timeframe consistent with the radiation therapy schedule (see, e.g., FIG. 1C). The nanoparticles can increase damage to cancer cells in conjunction with radiation therapy in several different ways. The immunoadjuvant can potentiate an immune response against the cancer cells, even cancer cells that are distant from the primary tumor (e.g., tumor cells that have metastasized or spread to other parts of the body). As the tumor cells die due to radiation exposure, they release antigens which can stimulate the immune response further. In addition, the nanoparticles themselves can interact with the radiation to produce tumor-toxic physical effects, including photoelectrons (FIG. 1B) and Cherenkov radiation, which can kill tumor cells either directly or through generation of free radicals or reactive oxygen species that are toxic to tumor cells. Further, the use of the immunoadjuvant-conjugated tumor cells of the invention can minimize the toxicity of radiotherapy by increasing its effectiveness, allowing a lower dose of radiation to be used.

Figure 1E:
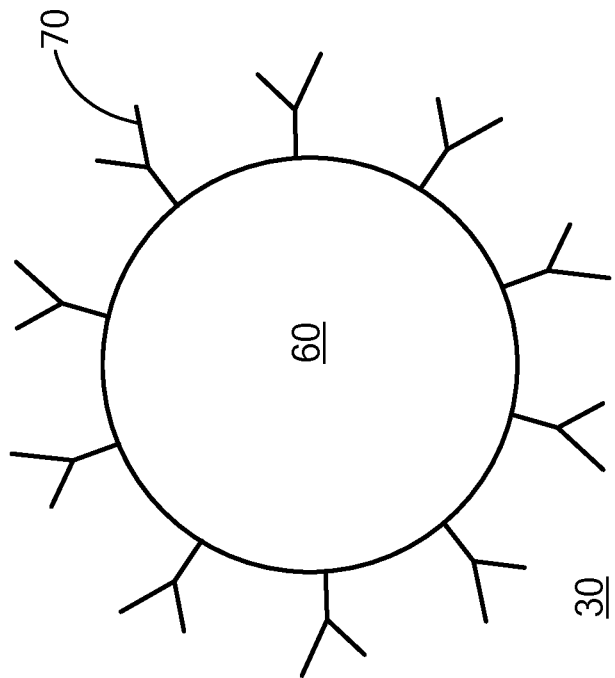
FIGS. 1D and 1E show schematic illustrations of biomaterials used in the process.
Figure 1D:
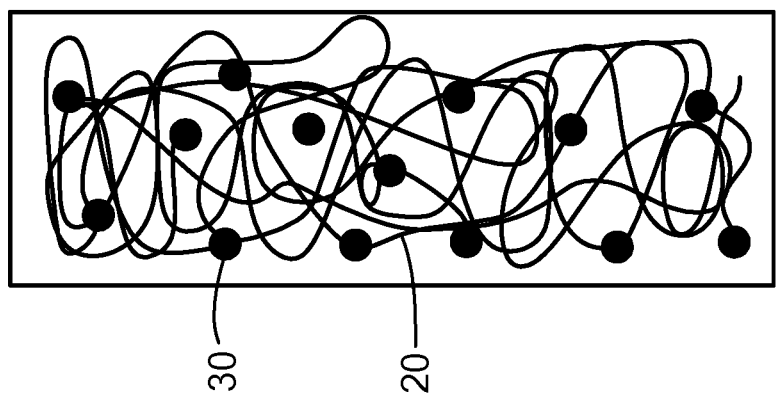

The invention provides biomaterials for placement within a tumor of a patient, or within a region of an organ or tissue suspected of containing one or more tumors or tumor cells. An illustration of an embodiment of an implant, such as a brachytherapy spacer, is shown in FIG. 1D. Implant 10 contains a plurality of metallic nanoparticles 30 dispersed in a solid matrix of biocompatible and biodegradable polymer molecules 20. An embodiment of a single metallic nanoparticle 30 is shown schematically in FIG. 1E. Metallic nanoparticle 60 is covalently conjugated at its surface to a plurality of immunoadjuvant molecules 70, such as antibodies to a cell surface receptor of an antigen presenting cell (APC).

As used herein, "metallic nanoparticle" encompasses nanoparticles containing metals in their pure state, metal oxides, and metal salts. The nanoparticles can contain either a single metal or an alloy of two or more metals, metal oxides, or metal salts. Preferably the metal is a metallic element with high atomic number (i.e., a "high Z" metal) that is effective at blocking X-rays. For example, metallic nanoparticles for use in the invention include or consist of gold, titanium oxide, iron oxide, zinc oxide, platinum, gadolinium, and combinations thereof. Preferably, the nanoparticles are radiopaque, i.e., block X-rays and can be visualized in an X-ray image of a patient in which the nanoparticles are implanted.

As used herein, "nanoparticle" refers to a particle having a length in its longest dimension of between about 1 nm and about 999 nm. Nanoparticles for use in the invention are preferably very small nanoparticles having an average size in the range from about 2 nm to about 15 nm. In various embodiments, the nanoparticles can have an average (e.g., diameter, or other largest extent in one dimension) from about 1 nm to about 10 nm, from about 5 nm to about 20 nm, from about 10 nm to about 30 nm, from about 15 nm to about 30 nm, from about 20 nm to about 40 nm, from about 25 nm to about 50 nm, from about 30 nm to about 60 nm, from about 40 nm to about 80 nm, from about 50 nm to about 100 nm, or from about 10 nm to about 100 nm, or from about 20 nm to about 150 nm. In the composition, a fraction of the metallic nanoparticles may have a size as indicated above. For example, at least 50%, at least 60%, at least 70%, at least 80%, at least 90%, at least 95%, at least 96%, at least 97%, at least 98%, or at least 99% of the nanoparticles may have sizes as indicated above. The metallic nanoparticles may be essentially spherical, or may have other shapes, such as rods, cylinders, cubes, ellipsoids, core-shell structures, or may be irregular in shape.

In certain embodiments, the nanoparticles are conjugated to a tumor-targeting moiety (also referred to as a "targeting moiety"). The tumor-targeting moiety can be a tumor-targeting ligand, peptide, protein, aptamer, oligonucleotide, antibody, cell adhesion molecule, or small molecule. A "small molecule" as used herein refers to an organic molecule, such as a drug or metabolite, which is less than 1000 in molecular weight, and which binds to a target, such as a protein or nucleic acid, within or on the surface of a tumor cell. For example, a tumor-targeting ligand can be folic acid, an antibody, such as a single-chain variable fragment antibody, a ligand for an epidermal growth factor receptor, transferrin, an arginylglycylaspartic acid (RGD) peptide, riboflavin, a prostate specific membrane antigen (PSMA) aptamer, or a galactose derivative. As nanoparticles conjugated to a targeting moiety are released from the degrading matrix material, they can bind to tumor cells, and are therefore useful for cancer diagnostic or therapeutic purposes.

Immunoadjuvants or other molecules, such as targeting moieties, can be covalently or non-covalently conjugated to the metallic nanoparticles by any of a variety of known methods and chemistries. For example, gold nanoparticles can be pre-functionalized with heterobifunctional polyethyleneglycols (PEGs) using a simple ligand exchange process. (Kumar et al. Translational Cancer Research. 2013, 2(4), 228-239) Three heterobifunctional PEGs, namely, methoxy-PEG-thiol (Mw: 2,000 Da), amine-PEG-thiol (Mw: 3,400 Da), and carboxymethyl-PEG-thiol (Mw: 2,000 Da), can be incubated alternatively with gold nanoparticles to obtain nanoparticles pre-functionalized with —OCH$_3$ (methoxy), —NH$_2$ (amino), and —COOH (carboxyl) groups. The free amino group on the nanoparticle surface can be used to covalently conjugate a protein or an imaging agent, e.g., using a succinimidyl ester of a fluorophore or a radiolabel in a basic medium. The carboxyl groups on the nanoparticle surface can be conjugated with an immunoadjuvant antibody or peptide, or a targeting agent, such as an antibody or peptide specific for a particular tumor type, using carbodiimide chemistry. The carboxyl groups can be activated using known water soluble cross linker 1-Ethyl-3-(3-dimethylaminopropyl)carbodiimide, which readily reacts with primary amines (e.g., on antibodies or peptides) to form stable amide bonds.

Any suitable biocompatible and biodegradable polymer can be used as the matrix material. In some embodiments, the matrix material is a polymer or co-polymer of lactide, glycolide, or a combination thereof. In other embodiments, the matrix material is a polyester of hydroxycarboxylic acids. In some embodiments, the matrix material is a polylactide, polyglycolide, polylactide co-glycolide (PLGA), polyester amide of glycolic or lactic acids, poly(N-isopropylacrylamide), polygalactin, polydioxanone, polyester, polyacrylate, polymethacrylate, polyvinyl alcohol, polyether, polyamine, chitosan, or a combination thereof.

As used herein, "immunoadjuvant" refers to a molecule that acts to accelerate, prolong, or enhance a desired immune response. Preferred immunoadjuvants are those that accelerate, prolong, or enhance an immune response against a tumor, and which can be covalently conjugated to a metallic nanoparticle. In some embodiments, the immunoadjuvant is a nonspecific stimulator of the immune response that promotes an environment conducive to immune stimulation. In an embodiment, the immunoadjuvant stimulates innate immune receptors. In other embodiments, the immunoadjuvant promotes and/or sustain an adaptive immune response. In some embodiments, the immunoadjuvant increases antigen presentation. In some embodiments, the immunoadjuvant enhances the uptake of tumor antigens by professional antigen-presenting cells. In some embodiments, the immunoadjuvant promotes the maturation and/or activation of an antigen-presenting cell. In some embodiments, the immunoadjuvant stimulates humoral antibody responses against tumor antigens. In some embodiments, the immunoadjuvant promotes the generation and/or activation of antigen-specific CD8+ T cells. In some embodiments, the immunoadjuvant promotes clonal T cell expansion. In some embodiments, the immunoadjuvant stimulates T lymphocyte and natural killer (NK) cells cytoxic response against antigens presented by tumor cells. In some embodiments, the immunoadjuvant stimulates CD4+ helper T-cell response. In some embodiments, the immunoadjuvant induces potent and long-lasting CD8+ T cell and NK cell responses. Preferred immunoadjuvants are molecules that can be conjugated to a metallic nanoparticle and which bind to and activate a receptor on or within a cell of the immune system.

The immunoadjuvant can be any compound that augments the potency of cancer therapy in order to generate or enhance a response to control the disease. For example, the immunoadjuvant can be an antibody, such as an anti-CTL4 antibody, GITR antibody, OX40 antibody, anti-PD1 antibody, anti-TIM3 antibody, anti-LAG3 antibody, or anti-CEACAM antibody. The immunoadjuvant can be a cytokine, such as IL-12, IL-7, IL-15, IL-21, GM-CSF, or IFN-gamma. It can be a ligand (agonist) for a Toll-Like Receptor (TLR) or other molecule that activates these receptors, or it can be a stimulator of interferon genes (STING). Alternatively, the immunoadjuvant can be a bacterium-derived substance, such as a TLR-2/4 ligand (e.g., bacillus Calmette-Guérin and lipopolysaccharide), TLR-3 agonist (e.g., polyriboinosinic-polyribocytidylic acid, TLR-7/8 ligand (e.g., imidazoquinolines), TLR-9 ligand and CpG oligodeoxynucleotide. It can be a mineral adjuvant, such as alum salt. It can be a tensoactive agent, such as Quil-A or QS-21. It can be an α-galactosylceramide analog.

The composition is preferably injectable or implantable in a patient. The implant can have any suitable size and shape. In some embodiments, the composition is configured as, or is a component of, a brachytherapy spacer, a radiotherapy fiducial marker, a balloon applicator, a brachytherapy applicator, a transponder (e.g. BEACON transponder), or a gel, such as an injectable gel. Gels can include, without limitation, polyethylene glycol (PEG), polyacrylic acid (PAA), polyacrylamide, poly(N-isopropylacrylamide), hyaluronic acid, and combinations thereof.

In some embodiments, the implant can have a shape of a rod, a cylinder, a bar, a cube, a rectangle, a sphere, a shell, or an ellipse or ellipsoid. Rod-, cylinder-, or bar-shaped implants can have dimensions similar to the dimensions of a brachytherapy spacer, fiducial marker, balloon applicator, brachytherapy applicator or transponder. In some embodiments, the implant is elongated and can have a length ranging from about 2 mm to about 8 mm, and a diameter or shortest width ranging from about 0.5 mm to about 1.5 mm. In some embodiments, the diameter is about 0.8 mm. In some embodiments, the implant is elongated and has an aspect ratio of shortest dimension to longest dimension ranging from 0.05 to 0.75. In some embodiments, the diameter can be sized to fit within a brachytherapy needle, such as an 18 G needle. In some embodiments, the implant is essentially spherical and have a diameter from about 4 cm to about 6 cm. In some embodiments, the implant is ellipsoidal and have a largest dimension from about 5 cm to about 7 cm, and a shortest dimension from about 5 cm to about 6 cm. In some embodiments, the implants are formed in shapes that correspond to the shapes of brachytherapy spacers, fiducial markers, balloon applicators, brachytherapy applicators and transponder used in radiotherapy techniques. The injection or implantation can be performed according to routine procedures known in the art. Once in place, the implant or injected material should gradually release the nanoparticles into the tumor as the matrix material degrades. Implantation incurs no additional inconvenience to a patient already undergoing radiotherapy or brachytherapy.

In some embodiments, the composition further includes a therapeutic agent dispersed within the matrix material in addition to the nanoparticles, thus providing an additional mechanism for treating cancer, and offering a further synergistic effect. The therapeutic agent can be an anti-cancer drug, such as for example, docetaxel, paclitaxel, doxorubicin, cisplatin, or gemcitabine, an anti-androgen compound, a small molecule signaling pathway inhibitor, or a combination thereof. Anti-androgen compounds can include, for example, enzalutamide, flutamide, nilutamide, bicalutamide, abiraterone acetate, cyproterone acetate, megestrol acetate, chlormadinone acetate, spironolactone, canrenone, drospirenone, dienogest, norgestimate, ketoconazole, or cimetidine. Small molecule signaling pathway inhibitors can include, for example, P13K inhibitors, PARP inhibitors, or P13K/AKT/mTOR pathway inhibitors. The therapeutic agent can also be released from nanoparticles, liposomes, polymersomes, or other carriers, providing a dual release mechanism.

Another aspect of the invention is a method of treating cancer. The method includes injecting or implanting a composition of the invention, or a device including the composition, into a tumor or into a region of an organ or tissue that contains tumor cells in a patient in need thereof. In some embodiments, a brachytherapy spacer, radiotherapy fiducial marker, balloon applicator, brachytherapy applicator, transponder, or gel including or formed of the composition is injected or implanted. In some embodiments, the method further includes performing radiation therapy on the patient. In some embodiments, brachytherapy is performed, and an implanted brachytherapy spacer includes a composition of the invention. In some embodiments, external beam therapy is performed and an implanted fiducial marker includes the instant composition. In some embodiments, the composition includes gold nanoparticles, and the radiation therapy produces electrons by the photoelectric effect. The radiation used to treat the patient may be adjusted if necessary to include an energy level suitable for producing free electrons from gold or another metal via the photoelectric effect. In other embodiments, the instant composition includes titanium nanoparticles, and the radiation therapy produces Cherenkov radiation. Such radiation is known to produce reactive radicals that are toxic to tumor cells. In some embodiments, the method is more effective at killing tumor cells than a method characterized by administration a non-conjugated or non-targeted form of said immunoadjuvant and radiation therapy.

In some embodiments the use of a nanoparticle-conjugated immunoadjuvant together with radiation therapy displays a synergistic effect, such as an abscopal effect, wherein tumor cells distant from irradiated tumor cells are killed. The abscopal effect may promote tumor growth suppression of a non-irradiated tumor that is at least 5%, at least 10%, at least 20%, at least 30%, at least 40%, at least 50%, at least 60%, at least 70%, at least 80%, at least 90%, or at least 95% of the tumor growth suppression of an irradiated tumor within the same subject. The abscopal effect may also promote tumor growth suppression of a non-irradiated tumor in a subject treated with the composition that is at least 5%, at least 10%, at least 20%, at least 30%, at least 40%, at least 50%, at least 60%, at least 70%, at least 80%, at least 90%, or at least 95% of the tumor growth suppression of non-irradiated tumors of a subject who has been treated with radiation therapy only. The abscopal effect may also promote tumor growth suppression of a non-irradiated tumor in a subject treated with the instant composition that is at least 5%, at least 10%, at least 20%, at least 30%, at least 40%, at least 50%, at least 60%, at least 70%, at least 80%, at least 90%, or at least 95% of the tumor growth suppression of irradiated tumors of a subject who has been treated with non-conjugated immunoadjuvant only. The instant invention may generate an abscopal response (i.e., tumor growth suppression of a second, non-irradiated tumor) in at least 5%, at least 10%, at least 20%, at least 30%, at least 40%, at least 50%, at least 60%, at least 70%, at least 80%, at least 90%, or at least 95% of the subjects treated with a composition of the invention and radiation therapy in a first, irradiated tumor.

In some embodiments of the method, the patient's immune response against the tumor or tumor cells is enhanced. In some embodiments, the method may also increase survival time or disease-free survival time of the patient. Without being bound by any particular theory, it is believed that the combination of radiotherapy with local administration of immunoadjuvant increases survival by enhancing the immune memory against tumor antigens. In some embodiments, survival is increased by at least 5%, at least 10%, at least 20%, at least 30%, at least 40%, at least 50%, at least 60%, at least 70%, at least 80%, at least 90%, or at least 100% longer than in subjects not treated with a composition of the invention with radiation therapy.

The metallic nanoparticles increase the effectiveness of radiotherapy against local tumor cells, allowing for lower doses of radiotherapy to be effective against said tumor cells. In some embodiments, the dose of radiation is less than would be administered for radiation therapy alone. The invention allows for the radiation dose to be reduced by at least 10%, at least 20%, at least 30%, at least 40%, at least 50%, at least 60%, at least 70%, at least 80%, or at least 90% compared to the dose that what would otherwise be required to achieve the same decrease in tumor size or the same tumor growth suppression with radiotherapy in the absence of a composition of the present invention.

In some embodiments, the radiation therapy treatment planning or segmentation is marginless, i.e., it obviates the need for margins around the tumor to be irradiated. Such margins normally include clinical target volume, internal target volume or planning target volume segmentation/contouring. Currently, radiation therapy requires inclusion of such margins to account for geometrical uncertainties regarding the target volume, such as those derived from individual variabilities in organ size and shape, or variation in the organ positioning each time the patient is placed on a treatment table. Marginless radiation therapy allows for the dose of radiation applied to healthy tissue surrounding the tumor cells to be minimized or eliminated.

The release of the nanoparticles from the matrix material can be customized by modifying the polymer degradation rate to release the nanoparticles over a period of time. For example, the degradation rate can be controlled by varying one or more of, for example, the degree of cross-linking in the polymer matrix material, the molecular weight of the polymer matrix material, the size and concentration of the nanoparticles, or the inclusion or concentration of a binder material. The release rate also can be controlled by the inclusion of an inert material such as silica or a bone material such as hydroxyapatite, a calcium salt, or a phosphate salt. In some embodiments, for example, the release rate can be selected to continue beyond the duration of a course of radiotherapy treatments. In some embodiments, the release duration can be from 1 to 5 days, 1 to 10 days, 1 to 20 days, 1 to 60 days, or 1 to 120 days. In some embodiments, the method further includes applying electromagnetic or acoustic waves to the patient following injection or implantation, so as to activate and/or accelerate degradation of the biodegradable polymer of the composition. The implants can also be customized to different patients or treatment schedules by varying the degradation rate of the polymer matrix material, and the nanoparticle size, shape, or functionalization. Nanoparticles can themselves contain other nanoparticles, or the metallic nanoparticles can be embedded within microparticles or capsules, so as to provide a dual release profile.

Any cancer of a solid tissue can be treated with a composition or method of the invention. In some embodiments, the cancer is pancreatic cancer, lung cancer, prostate cancer, breast cancer, colorectal cancer, liver cancer, cervical cancer or other gynecologic cancer. In some embodiments, the cancer is metastatic cancer.

EXAMPLES

Example 1. Implantation and Release of Nanoparticle Composition

Figures 2A, 2B, 2C, 2D:
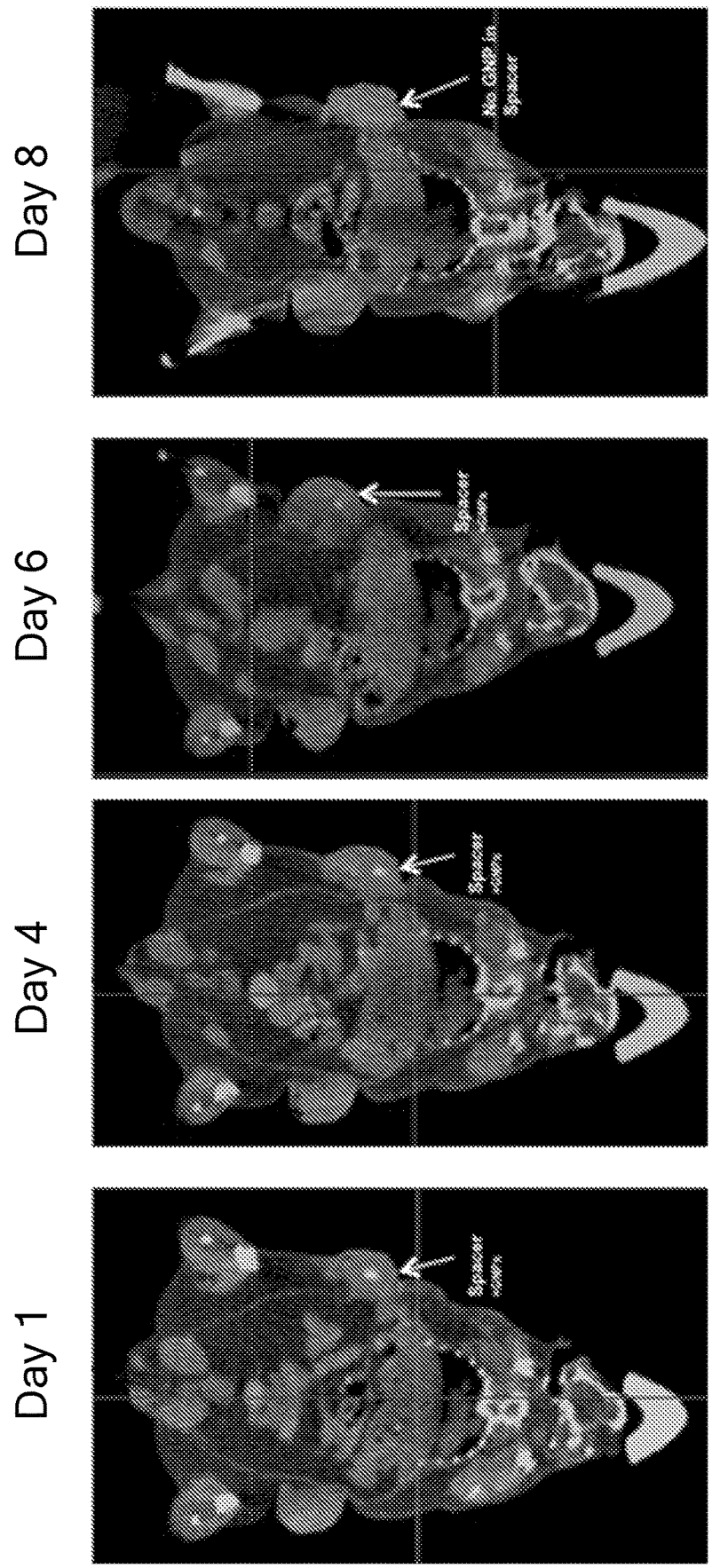
FIGS. 2A-D show computerized tomography (CT) images of tumor-bearing mice, which have received a tumor-implanted radiotherapy spacer containing gold nanoparticles conjugated with an immunoadjuvant dispersed within a biodegradable polymer matrix.

Pancreatic tumors were grown subcutaneously on the left and right flanks of C57BL/6 mice. The mice were randomized into four groups: a control group that received no treatment; a group that received radiotherapy only; a group that received immunotherapy (anti-CD40) only; and a group that received both radiotherapy and an implant containing anti-CD40 and metallic nanoparticles. FIGS. 2A-D show a tumor in a mouse containing an implant including the composition of the instant invention (gold nanoparticles conjugated to anti-CD40). The implant was radiopaque and could be clearly seen on day 1 post implantation (FIG. 1A). The implant gradually released its contents, including the gold nanoparticles, and it's size and opacity decreased until at day 8 it could no longer be detected (FIG. 2D).

Example 2. Synergistic Effect of Radiation Therapy and Immunoadjuvant Therapy

Figure 3:
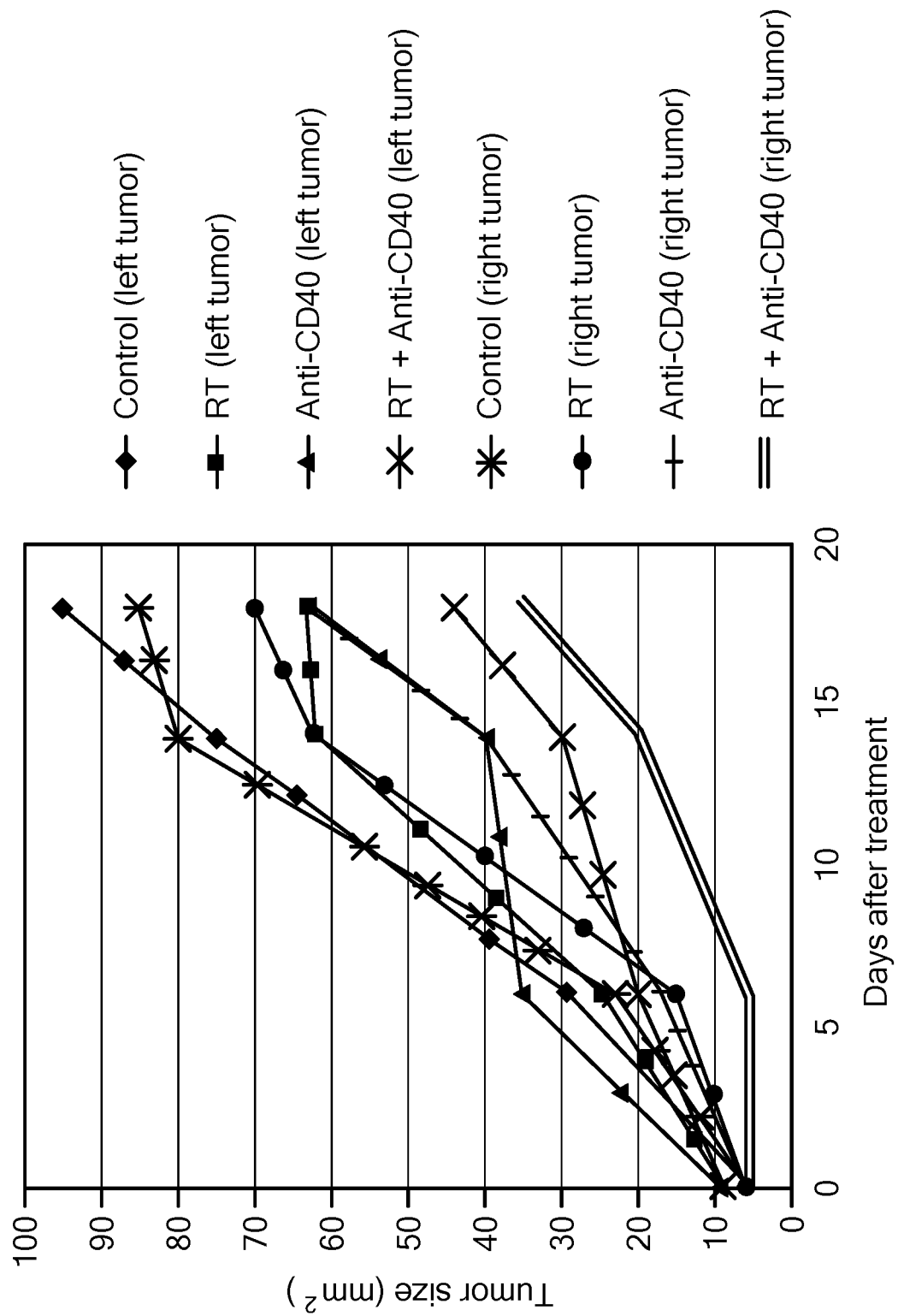
FIG. 3 shows mean tumor growth suppression results for four mouse groups which were treated as indicated on the graph at 19 days post tumor implantation. Tumors were implanted in both left and right flanks, but only tumors in the left flank were treated.

Tumors were grown in mice as in Example 1, and the mice were treated at 19 days after tumor implantation; only the left flank tumors or the right flank tumors were treated on each mouse. Treatment involved either radiation therapy (RT) alone, anti-CD40-conjugated gold nanoparticles alone, or a combination of radiation therapy and anti-CD40-conjugated gold nanoparticles. The results are shown in FIG. 3. Relative to the controls, the largest tumor growth suppression was observed in mice treated with both radiotherapy and the anti-CD40 nanoparticle composition. An abscopal response was also observed: 18 days after treatment, the untreated right side tumors of mice treated with the composition of the instant invention showed 63% tumor growth suppression relative to controls (FIG. 3).

Example 3. Abscopal Effect on Non-Irradiated Tumors

Figure 4:
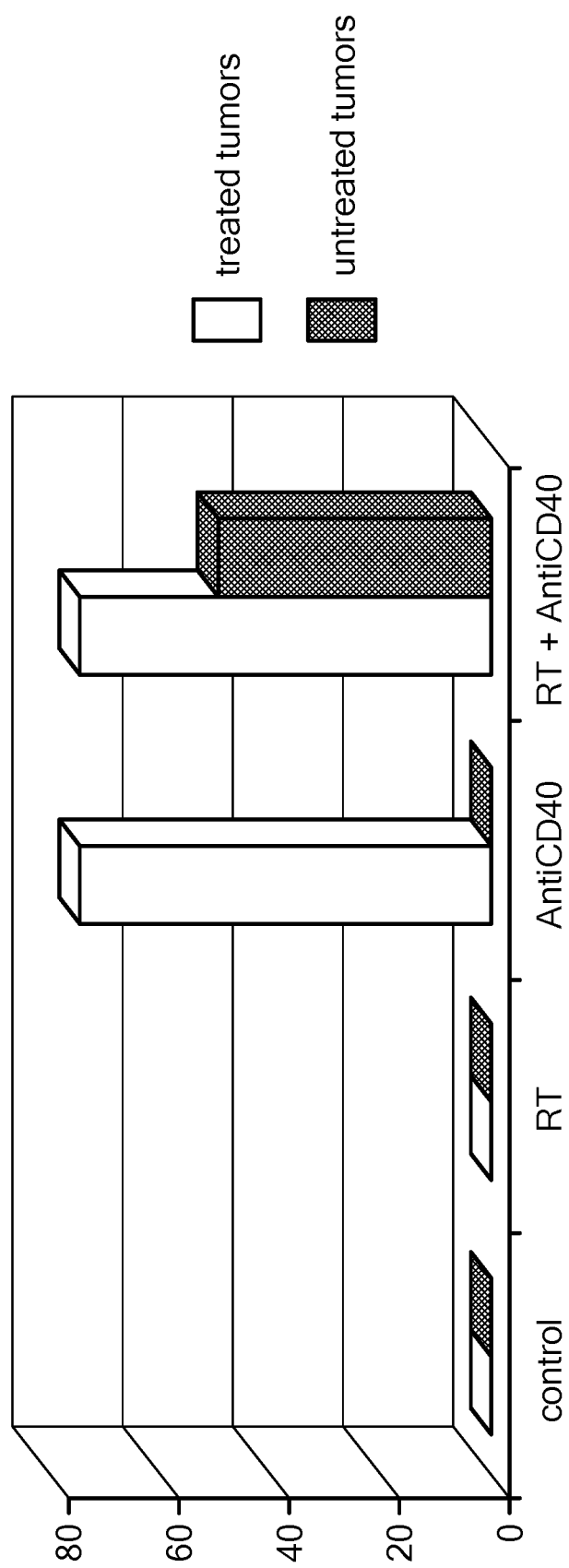
FIG. 4 shows the percentage of mice that showed complete tumor regression 18 days after beginning treatment. Four groups of mice were treated fat 12 days post tumor implantation. Tumors were implanted in both left and right flanks, but only tumors in the left flank were treated.
Figure 5:
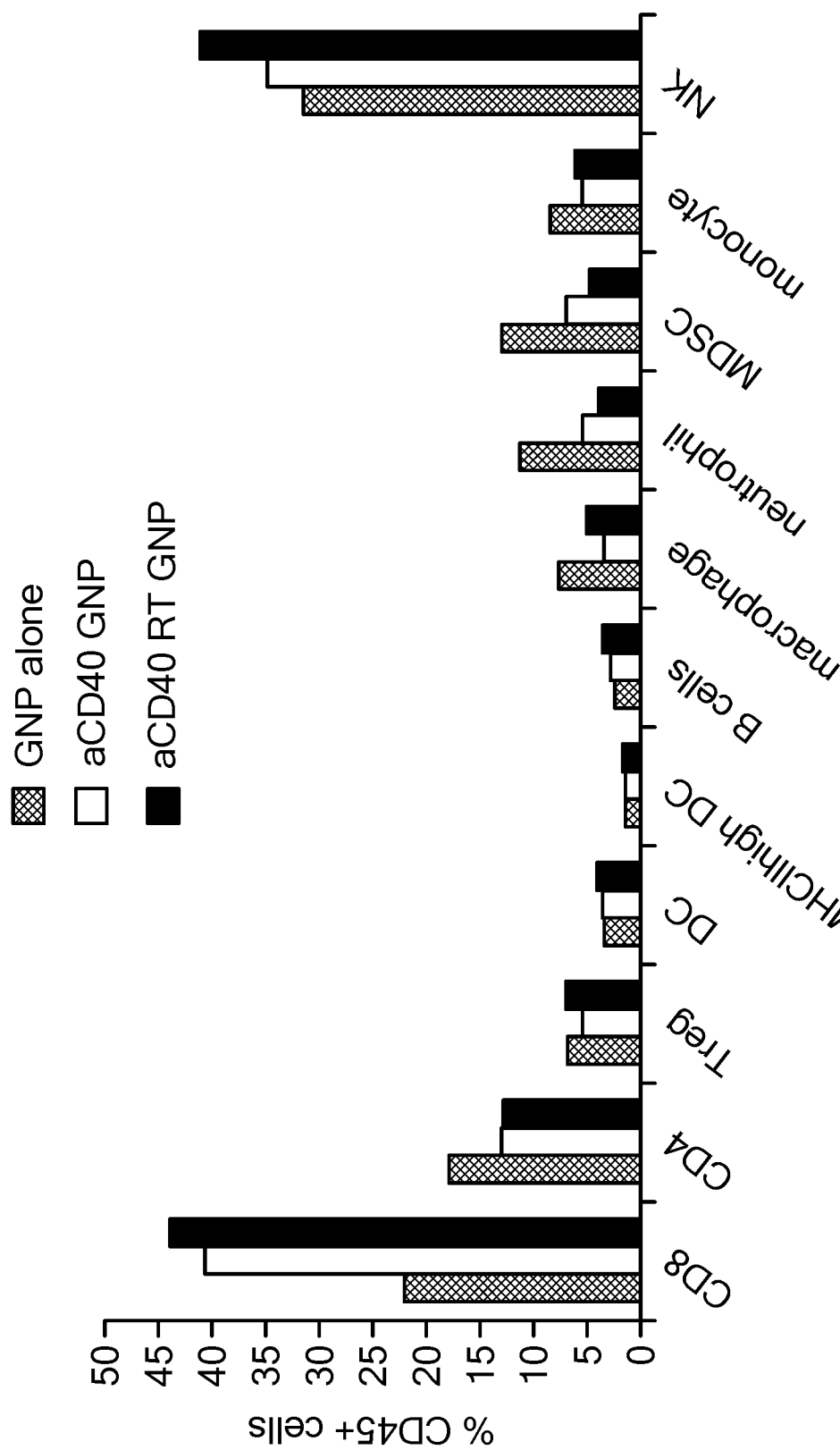
FIG. 5 shows the infiltration of various immune cells in untreated right flank tumors, following treatment of left flank tumors as indicated with gold nanoparticles alone (left hand bar of each group), gold nanoparticles conjugated with anti-CD40 antibodies (middle bar of each group), or gold nanoparticles conjugated with anti-CD40 antibodies plus radiation therapy (right hand bar of each group).

Tumors were grown in mice as in Example 1, and the mice were treated at 11 days after tumor implantation; only the left flank tumors were treated. Treatment modalities were the same as in Example 2. Over 50% of mice with one tumor treated by both radiotherapy and the anti-CD40 nanoparticle composition showed an abscopal response, i.e., they showed complete tumor regression in the untreated right flank tumor (FIG. 4). Meanwhile, such regression was not observed for any mice in the control group or the groups treated with radiation therapy alone or immunotherapy alone. When combining radiation therapy with the anti-CD40 nanoparticle composition, an increase in CD8+ T cells also was observed in the untreated (right flank) tumors (FIG. 5). A decrease also was observed in most myeloid cell types, particularly neutrophils and myeoloid-derived suppressor cells (MDSCs), and no apparent phenotypic change was observed in dendritic cell populations either within the tumor or in draining lymph nodes from the irradiated site.

As used herein, "consisting essentially of" allows the inclusion of materials or steps that do not materially affect the basic and novel characteristics of the claim. Any recitation herein of the term "comprising", particularly in a description of components of a composition or in a description of elements of a device, can be exchanged with "consisting essentially of" or "consisting of".

While the present invention has been described in conjunction with certain preferred embodiments, one of ordinary skill, after reading the foregoing specification, will be able to effect various changes, substitutions of equivalents, and other alterations to the compositions and methods set forth herein.

What is claimed is:

1. A composition for use in radiological diagnosis and/or therapy of cancer, the composition comprising metallic nanoparticles conjugated with an immunoadjuvant, the nanoparticles dispersed within a biodegradable polymer matrix.

2. The composition of claim 1, wherein the nanoparticles comprise or consist of gold, titanium oxide, iron oxide, zinc oxide, platinum, or gadolinium.

3. The composition of claim 1, wherein the nanoparticles are radioopaque.

4. The composition of claim 1, wherein the nanoparticles have a size from about 2 nm to about 15 nm.

5. The composition of claim 1, wherein the immunoadjuvant is granulocyte-macrophage colony-stimulating factor (GM-CSF), anti-CD40 antibodies, programmed death 1 (PD-1) receptor antibodies, anti-cytotoxic T-lymphocyte antigen 4 (CTLA-4) antibodies, glucocorticoid-induced tumor necrosis factor receptor (GITR) antibodies, OX40 antibodies, T-cell immunoglobulin and mucin-domain containing-3 (TIM3) antibodies, lymphocyte activation gene 3 (LAG3) antibodies, carcinoembryonic antigen-related cell adhesion molecule (CEACAM) antibodies, interleukin-12 (IL-12), Toll-like receptor (TLR) ligands, Stimulator of interferon genes (STING) agonists, or combinations thereof.

6. The composition of claim 1, wherein the biodegradable polymer matrix comprises polylactide, polyglycolide, polylactide co-glycolide, polyester amides of glycolic or lactic acids, poly(N-isopropylacrylamide), polygalactin, polydioxanone, polyester, polyacrylate, polymethacrylate, polyvinyl alcohol, polyether, polyamine, chitosan, silk, or combinations thereof.

7. The composition of claim 1 that is injectable or implantable in a patient.

8. The composition of claim 7 that is configured as, or is a component of, a brachytherapy spacer, a radiotherapy fiducial marker, a balloon applicator, a brachytherapy applicator, a transponder, or a gel.

9. The composition of claim 8, wherein the composition is configured as an implant, and the implant size is from about 3 mm to about 5 mm in length and from about 0.5 mm to about 1.5 mm in diameter.

10. The composition of claim 1, wherein the nanoparticles are in the form of spheres, rods, cubes, ellipsoids, or core-shell structures.

11. The composition of claim 1, wherein the nanoparticles are further conjugated to a targeting-moiety, and wherein the targeting-moiety is folic acid, antibodies including single-chain variable fragment antibody, ligands for an epidermal growth factor receptor, transferrin, an RGD peptide, tumor-specific small molecules, hyaluronic acid, riboflavin, PSMA aptamers, galactose derivatives, or combinations thereof.

12. The composition of claim 1 further comprising an antitumor agent, and wherein the antitumor agent is docetaxel, paclitaxel, gemcitabine, cisplatin, doxorubicin, small molecule signaling pathway inhibitors including PI3K inhibitors, PARP inhibitors, and PI3K/AKT/mTOR pathway inhibitors, or combinations thereof.

13. A method of treating cancer, the method comprising injecting or implanting the composition of claim 1 or a device comprising said composition into a tumor or into a region comprising tumor cells in a patient in need thereof.

14. The method of claim 13, wherein a brachytherapy spacer, radiotherapy fiducial marker, a balloon applicator, a brachytherapy applicator, a transponder, or gel comprising the composition is injected or implanted.

15. The method of claim 13, further comprising performing radiation therapy on the patient.

16. The method of claim 15, wherein the radiation therapy is brachytherapy and an implanted brachytherapy spacer comprises said composition, wherein the radiation therapy is external beam therapy and an implanted fiducial marker comprises said composition; wherein the radiation therapy produces electrons by a photoelectric effect and the said composition comprises gold nanoparticles; wherein the radiation therapy produces Cherenkov radiation and the said composition comprises titanium oxide nanoparticles; or wherein the radiation therapy produces an abscopal effect.

17. The method of claim 13, wherein the patient's immune response against said tumor or tumor cells is enhanced.

18. The method of claim 13, further comprising applying electromagnetic or acoustic waves to the patient following injection or implantation, so as to accelerate or activate degradation of the biodegradable polymer of said composition.

19. The method of claim 13, wherein the cancer is pancreatic cancer, lung cancer, prostate cancer, breast cancer, colorectal cancer, liver cancer, cervical cancer or other gynecologic cancers.

20. The method of claim 13, wherein the cancer is metastatic cancer.

* * * * *